(12) United States Patent
Sproul

(10) Patent No.: US 6,832,988 B2
(45) Date of Patent: Dec. 21, 2004

(54) ULTRASONIC CANNULA SYSTEM

(75) Inventor: Michael E. Sproul, Tequesta, FL (US)

(73) Assignee: Yacmur, Ltd., Jupiter, FL (US)

( * ) Notice: Subject to any disclaimer, the term of this patent is extended or adjusted under 35 U.S.C. 154(b) by 23 days.

(21) Appl. No.: 10/356,426

(22) Filed: Jan. 30, 2003

(65) Prior Publication Data

US 2004/0006347 A1 Jan. 8, 2004

Related U.S. Application Data

(63) Continuation-in-part of application No. 10/190,044, filed on Jul. 5, 2002, now Pat. No. 6,780,191.

(51) Int. Cl.[7] .................................................. A61B 8/14
(52) U.S. Cl. ....................................................... 600/459
(58) Field of Search ................................ 600/407–472; 367/7, 11, 130; 73/725, 726

(56) References Cited

U.S. PATENT DOCUMENTS

| | | |
|---|---|---|
| 5,167,619 A | 12/1992 | Wuchinich |
| 5,725,494 A | 3/1998 | Brisken |
| 5,759,154 A * | 6/1998 | Hoyns .......................... 600/458 |
| 5,820,552 A * | 10/1998 | Crosby et al. .............. 600/407 |
| 5,976,105 A | 11/1999 | Marcove et al. |
| 6,019,724 A * | 2/2000 | Gronningsaeter et al. ... 600/439 |
| 6,048,346 A | 4/2000 | Reiley et al. |
| 6,241,734 B1 | 6/2001 | Scribner et al. |
| 6,273,916 B1 | 8/2001 | Murphy |

* cited by examiner

Primary Examiner—Ali Imam
(74) Attorney, Agent, or Firm—McHale & Slavin, P.A.

(57) ABSTRACT

A surgical kit for inserting a biological material into a portion of the skeletal bone by a minimally invasive technique has several components which are manually operated using a universal tool. The kit includes a docking needle used as a guide for placing a cannula in a bone. The tool has a spring loaded hinged connection for temporarily attaching to the other components and which locks upon release of compression. An ultrasonic probe is inserted through the cannula for forming a cavity within the soft tissue of the bone. Treatment or support material is placed in the cannula and a plunger is inserted in the cannula. The universal tool is connected to the plunger and the material is expelled by telescopic movement of the plunger.

14 Claims, 4 Drawing Sheets

ULTRASONIC CANNULA SYSTEM

RELATED APPLICATIONS

This application is a continuation-in-part of application Ser. No. 10/190,044 now U.S. Pat. No. 6,780,191 filed Jul. 5, 2002, the entire contents of which are herein incorporated by reference.

FIELD OF THE INVENTION

This invention relates to orthopedic surgery and to an ultrasonic apparatus and process for minimal invasion of skeletal bones in the body for treatment and support.

BACKGROUND OF THE INVENTION

The use of cannulas to gain access to the interior regions of a patient's body is very old. In recent history, the use of the cannula in all types of surgery has gained wide acceptance. Heart catheterization and delivery of stints contributed to the increased popularity, as well as laproscopic surgery of all kinds. These techniques have reduced patient trauma, incidence of infection and hospital stays. These procedures have in common gaining access to the interior of the body by a small stab wound through which is inserted a cannula for maintaining a passageway. All sorts of other surgical implements may then traverse this passageway depending on the specific procedure to be performed on the patient.

Vertebroplasty was recently introduced to the medical arts as a percutaneous technique for repairing spinal compression fractures by injecting bone cement into the vertebral body. However, the technique quickly expanded to osteoporotic individuals that had been treated with narcotics and immobilization. The bone cement is used to shore up the collapsing vertebrae for support which relieves the pain associated with undue pressure on the nerves. This procedure rapidly gained acceptance as a substitute for open spinal surgery and vertebral microsurgery.

Radiologists and surgeons are involved in the procedure since the process is monitored by fluoroscopy and has the potential for leakage of the cement into the local blood stream. Some of the critical parameters of the procedure involve the mixing of the cement to an appropriate viscosity, ensuring that the cement is radio-dense for viewing, properly placing the injector inside the cancellous portion of a vertebra, and rigorously controlling injection pressure and quantity. See "Vertebroplasty: Dangerous Learning Curve," *START-UP*, June 2001.

DESCRIPTION OF THE PRIOR ART

U.S. Pat. No. 6,273,916 to Murphy describes vertebroplasty, generally, as performed on a prepped and draped prone patient who has been injected with a local anaesthetic. A skin incision is made over the selected vertebrae and a needle is inserted in a posterior approach to engage the vertebral body. A suitable cement is prepared using a contrast medium, such as barium powder, mixed with methylmethacrylate powder, and a monomer liquid. The cement (PMMA) becomes unworkable within 4 to 11 minutes from mixing.

Cement is injected into the vertebrae, while visualized by lateral and anterior-posterior X-ray projection fluoroscopy imaging. The injection is halted if the cement starts to extend into unwanted locations, such as the disc space or towards the posterior quarter of the vertebral body where the risk of epidural venous filling and spinal cord compression is greatest. If no unwanted migration is detected, the injection continues until the vertebrae is adequately filled. The amount of cement injected may vary considerably, e.g. from 4 to 36 cc.

Reiley et al, U.S. Pat. No. 6,048,346, teach a posterior-lateral approach for accessing the interior of the vertebrae for injecting bone cement or treatment substances or a combination of both. The bone cement is injected using a caulking gun-like device with a ram rod in the barrel.

In this procedure, the cement follows the cracks and crevices pre-existing in the vertebrae which may result in weak structural areas with little or no cement support between bony outcrops and/or migration of the cement outside the desired boundary through larger fissures before other areas are adequately filled.

Scribner et al, U.S. Pat. No. 6,241,734, teach the use of a balloon inflated within the intra-vertebral space to create a regular shaped void for application of a well shaped charge of cement with greater supporting characteristics. There are attendant risks of rupture of the inflated balloon while it is within the vertebrae. Scribner et al also teach the use of multiple components for gaining access to the intra-vertebral space.

Wuchinich, U.S. Pat. No. 5,167,619 discloses an ultrasonic handpiece used for reaming cement from a long bone preparatory to replacement of a prosthesis. Wuchinich recognizes that incidental contact between the ultrasonic probe and the interior of the bone surface is not injurious to the bone.

The use of an ultrasonic probe in the intervertebral disk is shown by Marcove et al, U.S. Pat. No. 5,976,105. The probe is not inserted within the vertebra body but is applied to the exterior tissues. The Marcove ultrasonic tip is vibrated longitudinally in the frequency range of 25 Khz to 60 Khz which is considered sufficient to soften body tissue. The energy is transmitted to the tip from a handpiece having an ultrasonic transducer connected to a wire extending through a cannula.

The use of an ultrasonic probe for treatment of blood clots is disclosed by U.S. Pat. No. 5,725,494 to Brisken. The vascular probe must be extremely flexible to follow the twists and turns of the blood vessels through which it traverses. The ultrasonic transducer is located at the leading end of the flexible probe.

What is needed in the art is a simple apparatus having several components operated by the same handle to perform cannulazation of skeletal bone including the formation, by ultrasound, of a defined intra-bone cavity for treatment deposits

SUMMARY OF THE INVENTION

Accordingly, it is an objective of this invention to teach a percutaneous system for surgery using ultrasonic vibration to shape or destroy tissue.

Also, it is an objective of the instant invention to teach a kit having a guide needle, cannulas, ultrasonic probe, several different cannula tips, a plunger, a clearing tool, a connector and a universal handle.

It is another objective of the instant invention to teach the formation of a cavity within bone or soft tissue, by ultrasonic energy, as well as, modulating and directing the ultrasonic energy to shape the cavity and to visualize the cavity.

It is yet another objective to teach a kit with several interchangeable tips to be fitted on the leading end of the cannula for different penetrations of the body.

It is a still further objective of the invention to teach a kit for orthopedic use to perform bone biopsy and to deliver a biological material to the cancellous portion of bone.

It is a further objective of the invention to teach manipulation of a biological material within the bone to change position, as well as, physical form It is yet another objective to teach a kit in which the universal tool has plural elements spring biased together and forms a temporary connection with the other components of the kit by operation of the spring bias.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DESCRIPTION OF THE INVENTION

Figure 1:
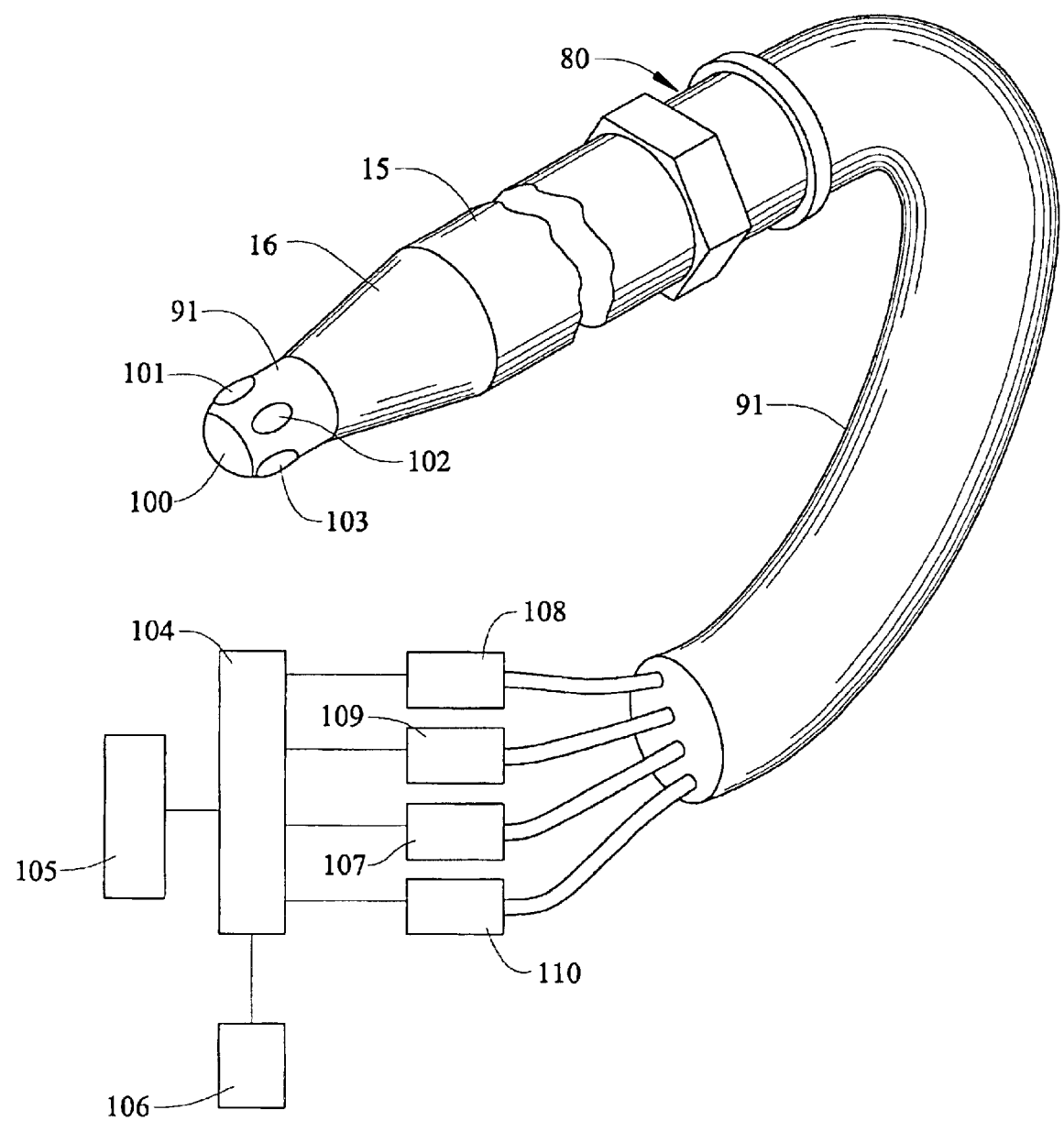
FIG. 1 is a schematic and partial perspective of the ultrasonic surgical system of this invention.

The ultrasonic surgical system, shown in FIG. 1, may have different utilitarian features, eg., the entire system may be housed in a free standing cabinet, either fixed or mobile. The system may be enclosed in a wall mounted or a table top cabinet. Or the different components could be separate and connected only by the various leads and tubes necessary for functional operation. Depending on the particular surgery to be performed and/or the anatomical location of the surgery, the system may be operated with less than all the components or some components inactive.

The leading end 91 of the tubular surgical implement is equipped to deliver ultrasonic energy, inject biological material, aspirate, and view the surgical field. Of course, these functions could be done sequentially through a single lumen in a catheter or the catheter can have multiple channels for simultaneous functions. As shown in FIG. 1, the ultrasonic energy is delivered by a transducer 100, the delivery of biological material is through lumen 101, the aspiration is through lumen 102, and visualization is through lumen 103. Each lumen of the catheter is connected to a controllable power unit for the respective function, for example, an ultrasonic transducer 107, a pressure pump 108, a suction pump 109, and camera and light source 110. Further, the visualization of the field may be by direct viewing by fiber optics and camera or computer enhanced imaging derived from ultrasound or sonar or similar devices.

The system may be operated by a control unit 104 in the form of a personal computer (PC) with a central processing unit (CPU); a memory; programming; an input device 105, such as a keyboard, joystick, touch screen; a display 106, such as a cathode ray tube (CRT), liquid crystal, etc.; and an output transmitting appropriate signals to the components. The control unit 104 of the system can modulate and aim the ultrasonic energy to destroy different density tissue and shape or limit the surgical field by controlling the ultrasonic transducer 105. The ultrasonic energy may be in the form of a directed beam which can be aimed by the control unit.

The introduction of biological material through lumen 101 results by direction of the pump through the control unit. Of course, the biological substance may be manually introduced through the lumen, if desired.

Figure 2:
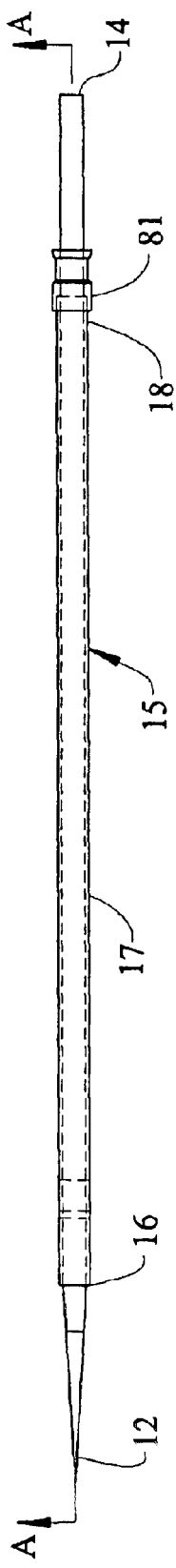
FIG. 2 is a perspective of the docking needle and a cannula removably telescoped together.
Figure 3:
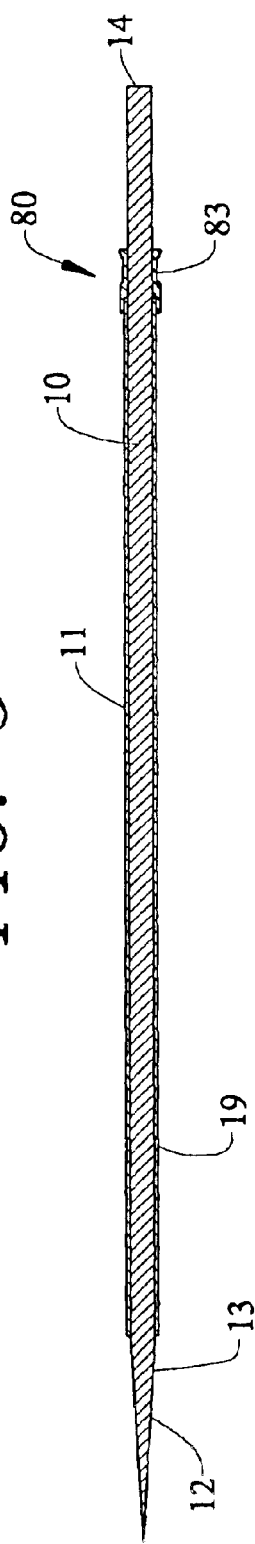
FIG. 3 is a cross section of the telescoped docking needle and cannula taken along line A—A of FIG. 1.
Figure 4:
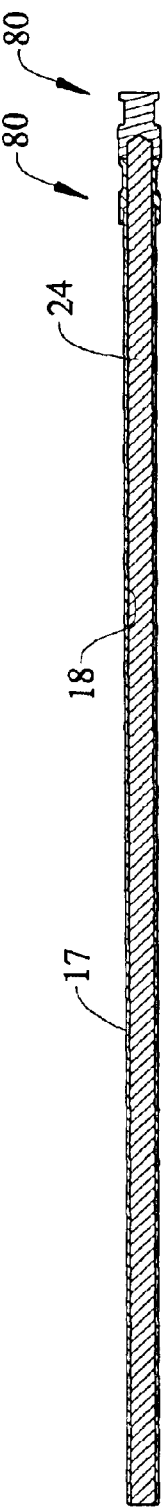
FIG. 4 is a longitudinal cross section of a cannula and a plunger.

The cannula system of this invention is in the form of a kit which, in one embodiment, includes a docking needle 10 with an elongated shaft 11, shown in FIGS. 2–4, having an insertion point 12 for penetration through the cutaneous layer of a patient. The point 12 passes through the skin, muscle and the hard shell of a bone into the softer cancellous bone material. The point 12 forms a tapered end portion with the base of the taper 13 smoothly merging into the shaft 11. The shaft may have a central bore 14 extending through the length of the needle. The bore may be eccentric in another embodiment (not shown).

The needle is of a size and material to withstand the compression required for insertion without deformation. The needle may be made of stainless steel, other metals, or suitable polymers. Normally, the insertion is performed manually by axial pressure at the trailing end of the needle to include striking the needle with a surgical hammer.

Figure 5:
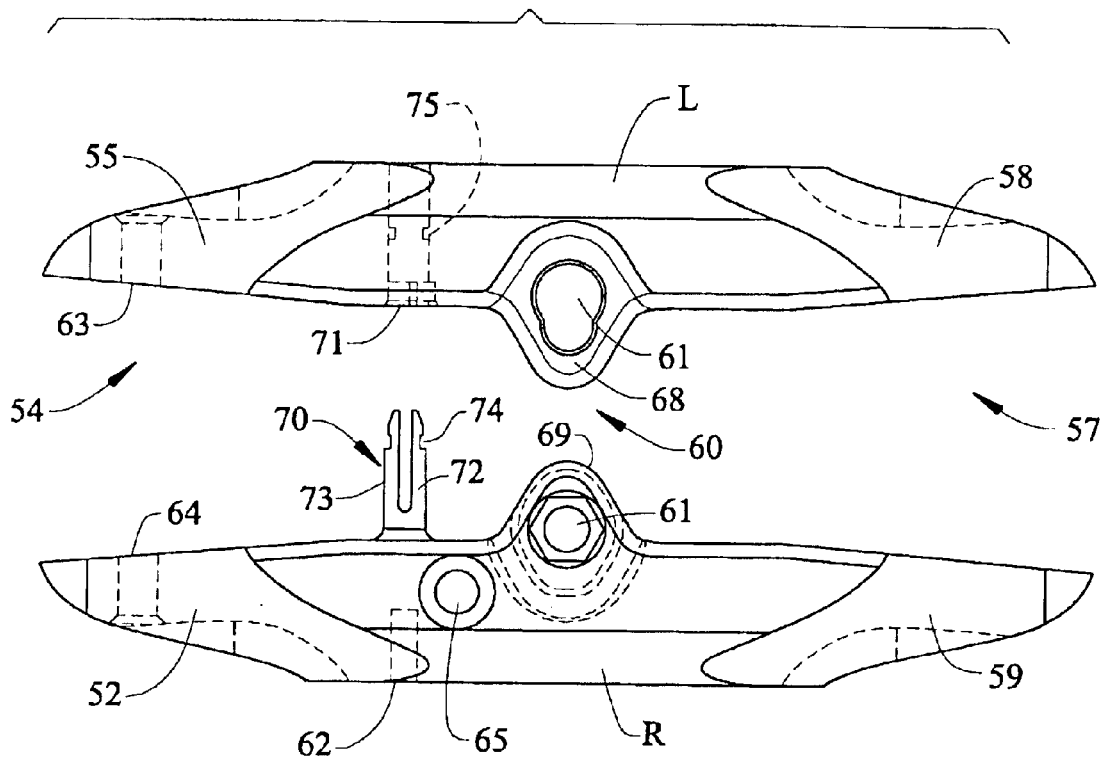
FIG. 5 is an exploded top view of the universal tool of this invention.

The tool or handle 50, shown in FIG. 5 is designed to fit on the trailing end of the needle for translating the manual axial pressure to the needle 10. The handle 50 is a universal tool for use with all the components of the kit. The needles and cannulas of the kit have a shaped tailing end that will fit into one of the blind bores on the handle or they will have a connector, as shown in FIG. 6, which cooperates with the eccentric lock of the handle 50.

Figure 8:
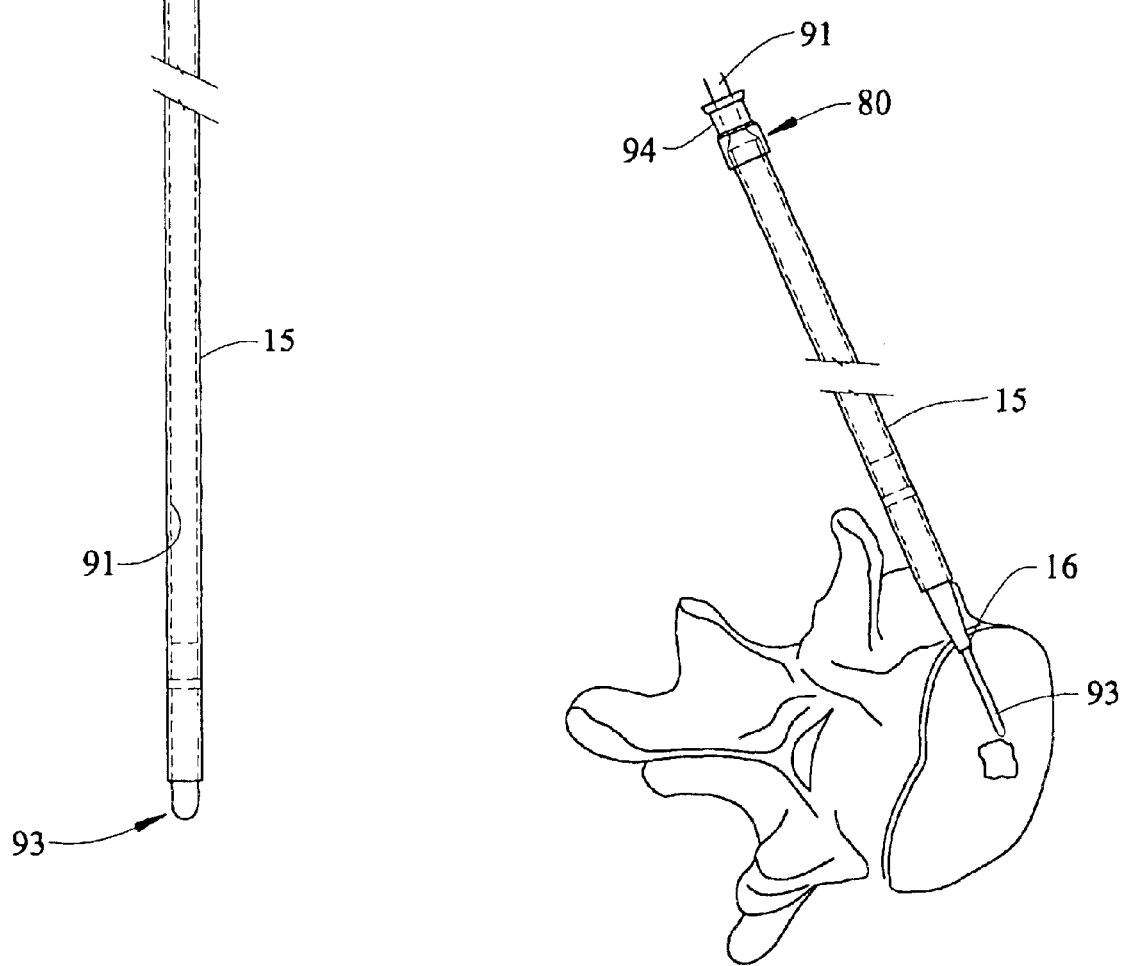
FIG. 8 is a perspective, partially in section, of a vertebra with and rigid ultrasonic probe therein.

Preferably, in vertebroplasty, the needle 10, as shown in FIG. 8, is inserted on a posterior-lateral tract, using X-ray fluoroscopy, to dock in a vertebrae anteriorly of the lateral process. Other approaches may be chosen by the surgeon. Regardless, of the orthopedic surgical procedure involved, the docked needle serves as a guide for the subsequent insertion of the cannulas of the system. Of course, in some applications, the needle and cannula may be inserted simultaneously.

In operation, a cannula 15 is telescoped over the docking needle 10 to provide a pathway for removal or delivery of material from the bone. The surgeon removes the handle 50 from the trailing end of the docking needle and connects the handle with the trailing end of the cannula. The leading end of the cannula is then placed over the trailing end of the needle. Axial pressure is applied to the cannula to slide the cannula along the needle to the desired location. Using fluoroscopy, the surgeon telescopes the cannula over the docking needle until the leading end of cannula and the leading end of the docking needle are flush or superimposed within the bone site thereby designating proper placement of the delivery cannula.

Figure 6:
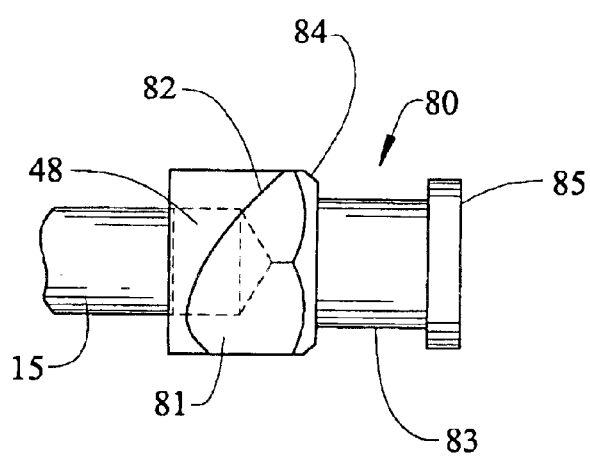
FIG. 6 is an enlarged view of the connector of this invention.

The trailing end 18 of the cannula has a connector 80, shown in FIG. 6, either removably affixed by internal threads 82, in the nature of a Leur-type fitting, or permanently connected to the shaft. The connector 80 has external planar surfaces 81 which provide a gripping surface for manipulating the cannula. In one embodiment, the connector has a hex-nut outer surface to prevent rotation within handle 50 although other configurations are a matter of choice. The connector 80 has a reduced diameter portion 83 between a shoulder 84 and a flange 85 to prevent longitudinal movement within the handle 50.

As shown in FIG. 5, the hinged eccentric lock 60 has a hinge 70 displaced laterally from the opening 61. The hinge post 70 formed on the R section of the handle is inserted into bore 71 on the L section. Both the bore 71 and the hinge post 70 are rectangularly shaped to provide an stabilized axis of rotation. As shown, the hinge post is bifurcated with two resiliently separated legs 72 and 73. The hinge post may be solid. The legs carry a circumferential slot 74 about their free ends. Upon assembly, the hinge post 70 is inserted into aperture 71 which has a smaller diameter than that of the hinge post. The aperture has a circular protrusion 75 about the interior wall. The protrusion 75 fits into the slot 74 to prevent the sections from separating after assembly. Of course, the R and L sections of the handle may be permanently fixed together forming an integral spring biased handle, eg., the hinge post and the bore may be autogenously bonded.

In the embodiment shown in FIG. 5, the R section of the universal tool 50 has a opening 61 therethrough surrounded by a columnar wall which ends in an extension 69. In another embodiment, (not shown) the extension 69 is omitted. The columnar wall has a circumferential slot into which the flange 68 is inserted. The flange 68 on the L section has an eccentric opening, a portion of which forms a part of the opening 61. Becasue the hinge is displaced from the flange, the flange has a lateral vector, as well as a rotational movement upon compression of the handle. When the R and L sections are assembled and the eccentric hinge is formed, a portion of the flange 68 obstructs the opening 61.

By compressing the universal handle, the jaws of the slit are forced closer together. The portion of the flange obstructing the bore 61 slides into registry with the columnar wall of the R section. This allows the connector 80 to telescope into the opening 61 and through the flange 68. When the manual compression is relieved, the flange 68 moves into the opening 61 and engages the reduced portion 83 of the connector 80 locking the cannula into the handle 50.

Once the cannula is telescoped over the needle to the desired location within the body, the handle is removed from the trailing end of the cannula and re-attached to the trailing end of the needle which extends beyond the trailing end of the cannula. Axial force is then applied in the opposite direction to remove the needle from the bone and the cannula. After the needle has been removed, the cannula bore 19 is open for either removing material for biopsy, for creating a space, or for dispensing a biological material for treatment.

Of course, the leading end 16 of the delivery cannula 15 may be modified to enhance the ability to cut through bone, particularly if a biopsy is necessary. Once the biopsy cannula 20 has been manipulated either rotationally or longitudinally or both by the handle 50 engaged with the connector 80, the handle is used to withdraw the cannula from the patient's body. A clearing tool is inserted into the bore 23. The clearing tool is advanced through the bore to push the tissue sample from the cannula.

If a biopsy is not required or after removal of the biopsy cannula, a delivery cannula 15 is telescoped over the docking needle, as described above. The delivery cannula is provided with a connector 80 at its trailing end. The longitudinal dimension of the connector is such that it fits within hinged eccentric lock 61 in the handle 50.

The tool or handle 50 is made from surgical stainless steel, liquid metal, or other magnetizable or non-magnetizable metals, or, preferably, molded or machined from a high impact polymer, such as polyethylene, polypropylene, NYLON or similar compositions capable of withstanding repeated sterilizations. The handle 50 has two elements, R and L, respectively, separated along a longitudinal center line 54. The handle is flexible and, preferably, resilient. The handle has a top surface 51, a bottom surface 52 and side walls defining a periphery 53. The left and right elements, R and L, of the handle are eccentrically hinged together at eccentric lock 60. The slit 54 has opposing jaws 55 and 56 which pivot about the spring biased center portion. The jaws 55 and 56 each have a bore 63 and 64, respectively, oriented in the same plane in which each jaw pivots.

Slit 54 extends through the side walls from the periphery toward the center portion with opposing jaws 58 and 59 which pivot about the spring biased eccentric lock 60.

By applying pressure on the opposing pairs of jaws of each slit, the jaws may approach with each other. When pressure is released, the respective pairs of jaws resiliently move away from each other. As illustrated, the slits are arranged to oppose each other.

A blind bore 62 is formed in the periphery of the handle for the purpose of engaging the trailing end of the docking needle. The shaft of the blind bore 62 is shaped to cooperate with the trailing end of the needle to provide rotation of the needle upon rotation of the handle. The surgeon manually grips the handle and applies longitudinal and/or rotational force through the handle to the needle to penetrate the soft tissue and bone of the patient. The handle may also provide a striking plate for receiving blows from a surgical hammer for driving the needle into the bone. Once the needle is properly docked in the bone, the handle is removed from the needle.

Blind bore 65 is of suitable size to accommodate the trailing end of the cannula fitted with a connector 80. The blind bore 65 has a larger diameter terminating with a shoulder 66 which will engage and stop the connector 80. A smaller diameter portion 67 of the bore continues above the shoulder to allow the trailing end of the docking needle to extend beyond the trailing end of the connector 80. Because the cannula is somewhat larger than the docking needle, the tip of the cannula may be sharpened to cut through the bone. A surgical hammer may be used to drive the delivery cannula, at least, through the hard outer shell of the bone. Once the cannula is located in the cancellous portion of the bone, the cannula may be removed from the blind bore 65.

The cannula with an attached connector 80 may then placed in the opening 61, of the handle. The connector 80 is engaged with the eccentric flange 68 to prevent longitudinal or rotational movement of the cannula within the handle. The surgeon telescopes the leading end of the cannula over the trailing end of the needle and again applies longitudinal force through the handle to the cannula to force the cannula through soft tissue and into the bone. As the cannula approaches the proper position in the bone, the trailing end 14 of the telescoped docking needle emerges from the trailing end of the cannula. When the trailing end of the needle 14 is level with the top surface 51 of the handle, the leading end 16 of the cannula is flush with the end of the needle. The top surface 51 of the handle and the trailing end 14 of the needle serve as a visual and tactile gauge, in the surgeon's hand, for properly placing the leading end of the cannula in the bone.

The handle 50 is then removed from the cannula and the jaws of slit 54 are pivoted to place the bores 63 and 64 in parallel. The trailing end of the needle is then inserted through bores 63 and 64. The pivoting pressure on jaws 55 and 56 is then released causing the bores to resiliently intersect engaging the shaft of the needle. Of course, the tool 50 may operate in reverse, with the pivoting pressure causing the jaws to close, in another embodiment. The needle is then removed from the cannula by use of the handle 50. After the needle is removed from the cannula the jaws are pivoted to release the shaft of the needle and free the handle.

Figure 7:
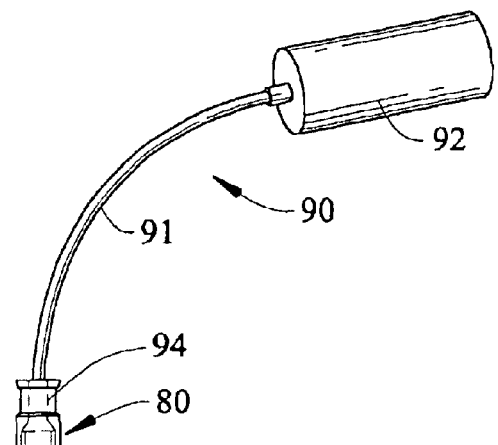
FIG. 7 is a side view of a flexible ultrasonic probe with the cannula and connector of this invention.

The ultrasonic apparatus 90 may now be introduced into the body through the cannula 15 which has penetrated the hard exterior of the bone, as shown in FIGS. 7–8. The probe 91 extends from the ultrasonic pulse generator 92 into the soft tissue inside the bone. The probe 91 is protected by the cannula with only the vibratory tip 93 exposed to the tissue. The probe, which is rigid in the longitudinal axis but may be transversely flexible, provides a degree of control of the ultrasonic tip by transmitting pressure from the surgeon directly to the tissue. Of course, the probe may be flexible with an ultrasonic transducer only on the vibrating tip, as shown in FIG. 7. The intensity and frequency of the ultrasonic pulses may be regulated by the pulse generator 92 to further control the effect of the tip upon the tissue. The ultrasonic probe may be modulated by suction in a multilumen catheter. The operation of the tip macerates or liquefies the soft tissue inside the hard bone thereby removing diseased or damaged tissue and leaving a void or pocket for receiving various treatment and/or reinforcement agents. Once the desired amount of tissue is destroyed, the ultrasonic probe 91 is withdrawn from the cannula. Because of the porous nature of the marrow and the fissures within structure, a cavity is formed within the soft tissue. As shown, the ultrasonic probe is used in vertebroplasty however, the device may be used in other procedures in other skeletal bones of the body. In one modification, the ultrasonic probe is separated from the pulse generator. In such case, the trailing end of the probe may have a fitting 94 to cooperate with the universal tool to aid in the withdrawal. Further, irrigation and aspiration catheters may be inserted through the cannula 15, if desired. A multilumen catheter may be used with separate lumen for the ultrasonic probe, irrigation, aspiration, illumination, and visualization.

The delivery cannula is now positioned to transmit or withdraw the biological material to/from the bone. In general, the biological substance may be either structural or a treating agent or a combination of both.

For example, the material may be selected from such groups of substances as BMP, bone morphogenic proteins, DBM, demineralized bone matrix, BOTOX and other viral vectors, any bone marrow aspirate, platelet rich plasma, composite ceramic hydroxyapatite, tricalcium phosphate, glass resin mixtures, resorbable highly purified polylacttides/polylactides-co-glycolides and others. The treating agent may include hormonal, antibiotic, anti-cancer, or growth factor substances, among others. The material may be liquid, powder, crystals, granules, paste, gel or other forms. In vertebroplasty, polymethylmethacrylate (PMMA) is the customary bone cement though other compounds may be used.

Regardless of the chemical make-up of the biological substance, this system preferably uses a high viscosity biological material delivered through the cannula at a low pressure. To accomplish this objective, after the delivery cannula is properly placed in the bone, it is filled with a biological material having a viscosity allowing it to flow into the cannula. The viscosity of some of the materials continues to increase within the cannula to reach a consistency acceptable to the surgeon. Other materials may be ready for use, when loaded in the cannula.

The surgeon inserts a plunger into the cannula 15 to express the biological substance into the cancellous portion of the bone. The plunger is fitted with a connector 80 and manipulated by handle 50. Both the plunger and the cannula 15 are telescoped together and the plunger is sized to substantially co-terminate with the leading end of the delivery cannula when both the connectors 80 are in contact. The diameter of the plunger is slightly less than the diameter of the cannula to provide telescoping movement for the system. The viscosity of the biological material will be such that the entire amount of the material will be expressed from the cannula. In this instance, the amount of biological material delivered is precisely measured to be the corresponding volume of the delivery cannula, for example, 4 cc.

Of course, the amount of biological material may be adjusted to a particular patient. This is accomplished through the continued fluoroscopic observance of the procedure. If more material is necessary in a particular procedure, the syringe used to load the delivery cannula may be utilized to pre-load the bone cavity before the plunger is inserted into the delivery cannula.

When the appropriate amount of biological material has been injected into the bone, the handle 50 is used to rotate and withdraw the plunger. Once the biological substance has begun to solidify, the handle is placed on the delivery cannula and twisted to rotate the cannula thereby separating the cannula from the substance. However, some substances will not harden or solidify. The ultrasonic probe may be re-introduced to manipulate the substance, in situ. For example, the biological substance may be injected as a powder or granules and subsequently transformed into a liquid within the bone. The cannula is subsequently withdrawn from the bone.

The kit of this invention may be produced in various sizes and combinations depending on the size of the patients and the procedures to be accomplished. For example, the kit may be used to deliver and remove balloons, stents and cages; pedicle screws and hardware, including laproscopic surgery; pouches and solutions for tissue augmentation; radioactive pellets, micro robots and chips; tracking and identification devices; medications; wires; laser systems; and the like.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

I claim:

1. A system for performing surgical procedures using ultrasound comprising a control unit having an output, said control unit having a central processing unit, a memory, a visual display and an input device, a probe adapted for insertion through a cannula into a surgical field, said probe having a leading end and a trailing end with a continuous outer wall, said output of said control unit connected to said trailing end of said probe, multiple lumen extending through said elongated probe from said leading end to said trailing end, an ultrasonic transducer connected to one of said multiple lumen, said output of said control unit adapted to modulate and direct said ultrasonic transducer.

2. A system for performing surgical procedures of claim 1 wherein a suction device is connected to another of said multiple lumen, said output of said control unit adapted to modulate and direct said suction device.

3. A system for performing surgical procedures of claim 2 wherein a third lumen of said multiple lumen delivers of a biological substance, said output of said control unit adapted to modulate and direct the delivery of said biological substance.

4. A system for performing surgical procedures of claim 3 wherein a fourth lumen of said multiple lumen is connected to a device to receive sound echoes from the surgical field, said control unit adapted to modulate and direct said echoes to provide a representation of said surgical field on said display.

5. A system for performing surgical procedures of claim 3 wherein a fourth lumen of said multiple lumen is optically connected to a device to visualize said surgical field on said display.

6. An ultrasonic surgical kit for forming a cavity in the interior of a skeletal bone by a minimally invasive procedure comprising at least one cannula, an ultrasonic probe having a trailing end and a tip, said cannula having a leading end for penetrating through cancellous bone within a body and a trailing end, said ultrasonic probe of a size to telescope through said cannula from said trailing end through said leading end, said probe having an exposed vibrating tip adapted to macerate soft tissue within the bone.

7. An ultrasonic surgical kit of claim 6 further comprising a universal tool, said tool having a body with a periphery and at least one slit through a portion of said body and extending to said periphery, spring biased jaws on opposite sides of said slit movable toward each other by compression of said tool, an opening formed in said body proximate to said slit, said opening adapted to accommodate said trailing end, said opening changing shape in response to said compression of said body whereby said cannula is locked into said tool upon release of said compression.

8. A surgical kit of claim 7 further comprising a plurality of different sized docking needles and different sized cannulas, each of said docking needles and said cannulas having a connector adapted to cooperate with said opening.

9. A surgical kit of claim 8 further comprising a blind bore in said body, said different sized docking needles having a pointed end and a shaped trailing end, said blind bore shaped to receive said shaped trailing end for inserting each of said docking needles into a patient whereby said tool is removed from said docking needle after said docking needle is inserted and said cannula is adapted to telescope over said docking needle.

10. A surgical kit of claim 8 further comprising a beveled tip on said docking needle, said tip having an oblong aperture.

11. A surgical kit of claim 7 further comprising a blind bore in said body, at least one docking needle having a pointed end and a shaped trailing end, said blind bore shaped to receive said shaped trailing end for inserting said docking needle into a patient whereby said tool is removed from said docking needle after said docking needle is inserted and said cannula is adapted to telescope over said docking needle.

12. A surgical kit of claim 7 further comprising said slit extending through said body and separating said body into two sections with opposed jaws, said sections connected together by an eccentric lock intermediate said periphery of said body, said eccentric lock having a resilient hinge providing a spring bias between said jaws, said opening extending through said tool adjacent said resilient hinge.

13. A surgical kit of claim 7 further comprising a connector on said trailing end of said ultrasonic probe, said connector adapted for connection in said opening.

14. A method of using an ultrasound surgical system comprising the steps of providing an ultrasonic transducer connected to an ultrasonic probe, providing a cannula, inserting said cannula into a skeletal bone of a patient, inserting said ultrasonic probe through said cannula into said bone, activating said ultrasonic probe to macerate bone tissue and form a cavity in said bone, withdrawing said ultrasonic probe, introducing a biological material through said cannula into said cavity, and withdrawing said cannula.

* * * * *